United States Patent
Boylan et al.

(10) Patent No.: US 7,128,757 B2
(45) Date of Patent: Oct. 31, 2006

(54) RADIOPAQUE AND MRI COMPATIBLE NITINOL ALLOYS FOR MEDICAL DEVICES

(75) Inventors: John F. Boylan, Murrieta, CA (US); Daniel L. Cox, Palo Alto, CA (US); Pamela A. Kramer-Brown, San Jose, CA (US)

(73) Assignee: Advanced Cardiovascular, Inc., Santa Clara, CA (US)

( * ) Notice: Subject to any disclaimer, the term of this patent is extended or adjusted under 35 U.S.C. 154(b) by 0 days.

(21) Appl. No.: 10/814,326

(22) Filed: Mar. 30, 2004

(65) Prior Publication Data

US 2004/0249447 A1 Dec. 9, 2004

Related U.S. Application Data

(63) Continuation-in-part of application No. 09/752,212, filed on Dec. 27, 2000, now Pat. No. 6,855,161.

(51) Int. Cl.
*A61F 2/90* (2006.01)
(52) U.S. Cl. ................... 623/1.18; 623/1.19
(58) Field of Classification Search ....... 623/1.15–1.22
See application file for complete search history.

(56) References Cited

U.S. PATENT DOCUMENTS

| | | | |
|---|---|---|---|
| 4,505,767 A | 3/1985 | Quin | |
| 4,631,094 A | 12/1986 | Simpson et al. | |
| 4,740,253 A | 4/1988 | Simpson et al. | |
| 4,770,725 A | 9/1988 | Simpson et al. | |
| 4,881,981 A | 11/1989 | Thoma et al. | |
| 5,002,563 A | 3/1991 | Pyka et al. | |
| 5,201,901 A | 4/1993 | Harada et al. | |
| 5,411,476 A | 5/1995 | Abrams et al. | |
| 5,465,717 A | 11/1995 | Imran et al. | |
| 5,486,183 A | 1/1996 | Middleman et al. | |
| 5,562,641 A | 10/1996 | Flomenblit et al. | |
| 5,630,840 A | 5/1997 | Mayer | |
| 5,632,746 A | 5/1997 | Middleman et al. | |
| 5,637,089 A | 6/1997 | Abrams et al. | |
| 5,641,364 A | 6/1997 | Golberg et al. | |

(Continued)

FOREIGN PATENT DOCUMENTS

EP 0 873 734 10/1998

(Continued)

OTHER PUBLICATIONS

U.S. Appl. No. 09/452,516, filed Dec. 1, 1999.

(Continued)

*Primary Examiner*—David H. Willse
(74) *Attorney, Agent, or Firm*—Finnegan, Henderson, Farabow, Garrett & Dunner LLP

(57) ABSTRACT

A radiopaque nitinol medical device such as a stent for use with or implantation in a body lumen is disclosed. The stent is made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The nitinol stent has improved radiopacity yet retains its superelastic and shape memory behavior and further maintains a thin strut/wall thickness for high flexibility. Another embodiment includes a balloon expandable stent made from a radiopaque and MRI compatible alloy such as nitinol and includes a ternary element selected from the group of chemical elements consisting of iridium, platinum, gold, rhenium, tungsten, palladium, rhodium, tantalum, silver, ruthenium, hafnium, osmium, zirconium, niobium, or molybdenum.

49 Claims, 4 Drawing Sheets

U.S. PATENT DOCUMENTS

| | | | |
|---|---|---|---|
| 5,643,312 | A | 7/1997 | Fischell et al. |
| 5,667,522 | A | 9/1997 | Flomenblit et al. |
| 5,690,644 | A | 11/1997 | Yurek et al. |
| 5,720,754 | A | 2/1998 | Middleman et al. |
| 5,843,244 | A | 12/1998 | Pelton et al. |
| 5,885,381 | A | 3/1999 | Mitose et al. |
| 5,891,191 | A | 4/1999 | Stinson |
| 5,902,317 | A | 5/1999 | Kleshinski et al. |
| 5,927,345 | A | 7/1999 | Samson |
| 5,951,793 | A | 9/1999 | Mitose et al. |
| 5,976,153 | A | 11/1999 | Fischell et al. |
| 5,989,280 | A | 11/1999 | Euteneuer et al. |
| 6,001,123 | A | 12/1999 | Lau |
| 6,004,330 | A | 12/1999 | Middleman et al. |
| 6,051,021 | A | 4/2000 | Frid |
| 6,059,810 | A | 5/2000 | Brown et al. |
| 6,068,623 | A | 5/2000 | Zadno-Azizi et al. |
| 6,137,060 | A * | 10/2000 | Avellanet ................. 174/128.1 |
| 6,171,334 | B1 | 1/2001 | Cox |
| 6,183,409 | B1 | 2/2001 | Armini |
| 6,190,332 | B1 | 2/2001 | Muni et al. |
| 6,210,312 | B1 * | 4/2001 | Nagy ............................ 600/3 |
| 6,217,567 | B1 | 4/2001 | Zadno-Azizi et al. |
| 6,312,454 | B1 | 11/2001 | Stockel et al. |
| 6,312,455 | B1 | 11/2001 | Duerig et al. |
| 6,325,824 | B1 | 12/2001 | Limon |
| 6,329,069 | B1 | 12/2001 | Azizi et al. |
| 6,375,628 | B1 | 4/2002 | Zadno Azizi et al. |
| 6,375,629 | B1 | 4/2002 | Muni et al. |
| 6,380,457 | B1 | 4/2002 | Yurek et al. |
| 6,419,693 | B1 | 7/2002 | Fariabi |
| 6,432,116 | B1 | 8/2002 | Callister et al. |
| 6,461,453 | B1 | 10/2002 | Abrams et al. |
| 6,468,230 | B1 | 10/2002 | Muni et al. |
| 6,572,646 | B1 * | 6/2003 | Boylan et al. ............. 623/1.12 |
| 6,582,461 | B1 * | 6/2003 | Burmeister et al. ........ 623/1.18 |
| 6,755,855 | B1 | 6/2004 | Yurek et al. |
| 6,786,984 | B1 * | 9/2004 | Hanada et al. .............. 148/421 |
| 2001/0049549 | A1 | 12/2001 | Boylan et al. |
| 2002/0082681 | A1 | 6/2002 | Boylan et al. |
| 2003/0055449 | A1 | 3/2003 | Lee et al. |

FOREIGN PATENT DOCUMENTS

| | | |
|---|---|---|
| EP | 0873734 A2 * | 10/1998 |
| WO | WO 97 24978 A | 7/1997 |
| WO | WO 02 051462 | 7/2002 |
| WO | WO 03 097148 | 11/2003 |

OTHER PUBLICATIONS

U.S. Appl. No. 09/572,352, filed May 17, 2000.

Foreign patent office search report and written opinion for International Application No. PCT/US2005/004698.

Yang, J.H. et al., *Stress-Induced transformation and Superelasticity in Ni-Ti-Nb Alloys*, Journal De Physique IV, pp. C8-771-776 (Dec. 1995).

Stockel, D. et al., *Superelastic.Ni-Ti-Wire*, Wire Journal International, pp. 45-50 (Mar. 1991).

Schetky, L.M., Shape Memory Alloys, *Scientific American*, pp. 74-82 (Nov. 1979).

Russell, S.M. et al., *Improved NiTi Alloys for Medical Applications*, Proceedings of the Second International Conference on Shape Memory and Superelastic Technologies, pp. 429-436, 1997.

Proft, J.L. et al., *The Mechanical Aspects of Constrained Recovery*, Raychem Corp., pp. 115-129 (1985).

Perkins, J., *Ti-Ni and Ti-Ni-X Shape Memory Alloys*, Metals Forum, vol. 3, pp. 153-163 (1981).

Pelton, A.R. et al., Optimisation of Processing and Properties of Medical Grade Nitinol Wire, *Min Invas Ther & Allied Technol 200*, 9(1), 107-118 (2000).

Otsuka, K. et al., *Shape Memory Effect*, Shape Memory Materials, p. 41 (1998).

Lindquist, P.G., Ph.D., Structure and Transformation Behavior of Martensitic Ti(Ni, Pd) and Ti(Ni, Pt) Alloys, *Unioversity of Illinois at Urbana-Champaign* (1988).

Lin, Z.C. et al., *The Study on Superelasticity of NiTiPt wire as a function of Application Temperature*, Technical Report, Guidant Corp., pp. 1-4 (Jun. 19, 2003).

Enami, K. et al. Effect of W addition on the Martensitic Transformation and Shape Memory Behavior of the TiNi-Base Alloys, *Journal De Physique IV*, vol. 5-C8, pp. 629-C86, Dec. 1995.

Duerig, T.W. et al., *Superelastic Nitinol for Medical Devices*, Medical Plastics and Biomaterials Magazine, pp. 1-14, Mar. 1997.

Duerig, T.W. et al., "An Engineers Perspective of Pseudoelasticity," *The Mechanisms of Pseudoelasticity*, 369-393.

* cited by examiner

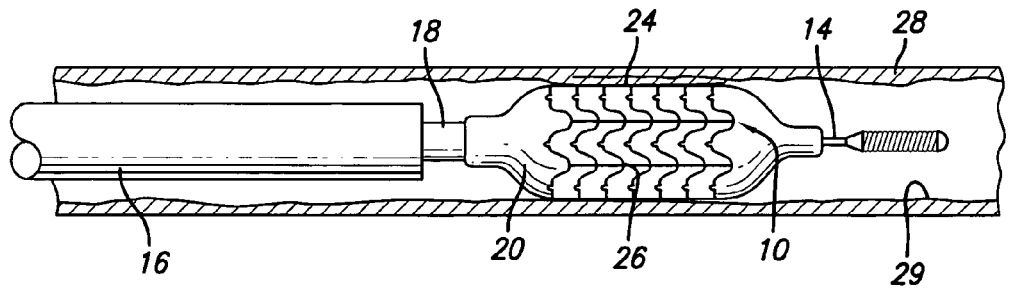
FIG. 1
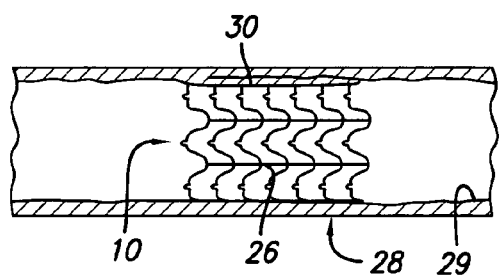
FIG. 2
FIG. 3
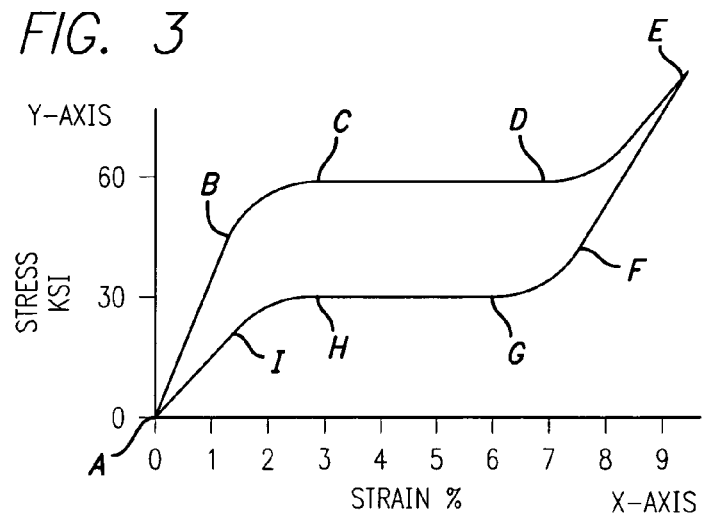

RADIOPAQUE AND MRI COMPATIBLE NITINOL ALLOYS FOR MEDICAL DEVICES

CROSS-REFERENCE TO RELATED APPLICATION

This application is a continuation-in-part of co-pending application Ser. No. 09/752,212 filed on Dec. 27, 2000, now U.S. Pat. No. 6,855,161, which is incorporated herein by reference.

BACKGROUND OF THE INVENTION

1. Field of the Invention

The present invention generally relates to self-expanding medical devices. More precisely, the present invention relates to self-expanding medical devices made of radiopaque nitinol that can be used in essentially any body lumen. Such devices include stents.

2. General Background and State of the Art

Stents are typically implanted in a body lumen, such as carotid arteries, coronary arteries, peripheral arteries, veins, or other vessels to maintain the patency of the lumen. These devices are frequently used in the treatment of atherosclerotic stenosis in blood vessels especially after percutaneous transluminal angioplasty (PTA) or percutaneous transluminal coronary angioplasty (PTCA) procedures with the intent to reduce the likelihood of restenosis of a vessel. Stents are also used to support a body lumen, tack-up a flap or dissection in a vessel, or in general where the lumen is weak to add support.

During PTCA procedures it is common to use a dilatation catheter to expand a diseased area to open the patient's lumen so that blood flows freely. Despite the beneficial aspects of PTCA procedures and its widespread and accepted use, it has several drawbacks, including the possible development of restenosis and perhaps acute thrombosis and sub-acute closure. This recurrent stenosis has been estimated to occur in seventeen to fifty percent of patients despite the initial PTCA procedure being successful. Restenosis is a complex and not fully understood biological response to injury of a vessel which results in chronic hyperplasia of the neointima. This neointimal hyperplasia is activated by growth factors which are released in response to injury. Acute thrombosis is also a result of vascular injury and requires systemic antithrombotic drugs and possibly thrombolytics as well. This therapy can increase bleeding complications at the catheter insertion site and may result in a longer hospital stay. Sub-acute closure is a result of thrombosis, elastic recoil, and/or vessel dissection.

Several procedures have been developed to combat restenosis and sub-acute or abrupt closure, one of which is the delivery and implanting of an intravascular stent. Stents are widely used throughout the United States and in Europe and other countries. Generally speaking, the stents can take numerous forms. One of the most common is a generally cylindrical, hollow tube that holds open the vascular wall at the area that has been dilated by a dilation catheter. One highly regarded stent used and sold in the United States is known under the tradename ACS Multi-Link Stent, which is made by Advanced Cardiovascular Systems, Inc., Santa Clara, Calif.

In expandable stents that are delivered with expandable catheters, such as balloon catheters, the stents are positioned over the balloon portion of the catheter and are expanded from a reduced diameter to an enlarged diameter greater than or equal to the inner diameter of the arterial wall by inflating the balloon. Stents of this type can be expanded to an enlarged diameter by deforming the stent, by engagement of the stent walls with respect to one another, and by one way engagement of the stent walls together with endothelial growth onto and over the stent.

Examples of intravascular stents can be found in U.S. Pat. No. 5,292,331 (Boneau); U.S. Pat. No. 4,580,568 (Gianturco); U.S. Pat. No. 4,856,516 (Hillstead); U.S. Pat. No. 5,092,877 (Pinchuk); and U.S. Pat. No. 5,514,154 (Lau et al.), which are incorporated herein by reference in their entirety.

The problem with some prior art stents, especially those of the balloon expandable type, is that they are often stiff and inflexible. These balloon expandable type stents are commonly formed from stainless steel alloys and the stents are constructed so that they are expanded beyond their elastic limit. As a result, such stents are permanently deformed by the inflation balloon beyond their elastic limits to hold open a body lumen and thus maintain patency of that body lumen. There are several commercially available balloon expandable stents that are widely used; they are generally implanted in the coronary arteries after a PTCA procedure mentioned earlier.

Stents are often times implanted in vessels that are closer to the surface of the body, such as in the carotid arteries in the neck or in peripheral arteries and veins in the leg. Because these stents are so close to the surface of the body, they are particularly vulnerable to impact forces that can partially or completely collapse the stent and thereby block fluid flow in the vessel. Other forces can impact balloon expandable stents and cause similar partial or total vessel blockage. For instance, under certain conditions, muscle contractions might also cause balloon expandable stents to collapse partially or completely. The collapse occludes the lumen and restricts blood flow in the vessel in which they are implanted.

Since balloon expandable stents are plastically deformed, once collapsed or crushed they remain so, permanently blocking the vessel. Thus, balloon expandable stents under certain conditions might pose an undesirable condition for the patient.

Self-expanding stents as the name implies self-expand through the properties of the material constituting the stent. The inflation force of a balloon catheter is usually not necessary to deploy this kind of stent.

Important applications including those mentioned above have prompted designers to seek out superelastic shape memory alloys to exploit the materials' properties in their self-expanding stents. Examples of applying superelastic nickel-titanium alloys to a self-expanding stent and other medical devices are disclosed in U.S. Pat. Nos. 4,665,906; 5,067,957; 5,190,546; and 5,597,378 to Jervis and U.S. Pat. No. 4,503,569 to Dotter. Another example is disclosed in European Patent Application Publication No. EP0873734A2, entitled "Shape Memory Alloy Stent." This publication suggests a stent for use in a lumen in a human or animal body having a generally tubular body formed from a shape memory alloy which has been treated so that it exhibits enhanced elastic properties. The publication further suggests use of specified ternary elements in a nickel-titanium alloy to obtain desired engineering characteristics.

Use of a ternary element in a superelastic stent is also shown in, for example, U.S. Pat. No. 5,907,893 to Zadno-Azizi et al. As a general proposition, there have been attempts at adding a ternary element to nickel-titanium alloys as disclosed in, for instance, U.S. Pat. No. 5,885,381 to Mitose et al.

Clearly, self-expanding, nickel-titanium stents are useful and valuable to the medical field. But a distinct disadvantage with self-expanding nickel-titanium stents is the fact that they are not sufficiently radiopaque as compared to a comparable structure made from gold or tantalum. For example, radiopacity permits the cardiologist or physician to visualize the procedure involving the stent through use of fluoroscopes or similar radiological equipment. Good radiopacity is therefore a useful feature for self-expanding nickel-titanium stents to have.

Radiopacity can be improved by increasing the strut thickness of the nickel-titanium stent. But increasing strut thickness detrimentally affects the flexibility of the stent, which is a quality necessary for ease of delivery. Another complication is that radiopacity and radial force co-vary with strut thickness. Also, nickel-titanium is difficult to machine and thick struts exacerbates the problem.

Radiopacity can be improved through coating processes such as sputtering, plating, or co-drawing gold or similar heavy metals onto the stent. These processes, however, create complications such as material compatibility, galvanic corrosion, high manufacturing cost, coating adhesion or delamination, biocompatibility, loss of coating integrity following collapse and deployment of the stent, etc.

Radiopacity can also be improved by alloy addition. One specific approach is to alloy the nickel-titanium with a ternary element. What has been needed and heretofore unavailable in the prior art is a superelastic nickel-titanium stent that includes a ternary element to increase radiopacity yet preserves the superelastic qualities of the nitinol.

The use of magnetic-resonance-imaging ("MRI") is also becoming more common, and imaging with this modality is of increasing importance. Current medical devices, such as stents, made of stainless steel produce a large MR imaging artifact, and diagnostics with MRI are more limited because of the image distortion produced near these stents. Alloys that are biocompatible, radiopaque and MRI compatible are not common, but the ability to use the same material under both of these imaging modalities is highly desirable. An alloy that is both radiopaque and MRI compatible will be referred to as an XMR alloy. Therefore, what is needed is a stent that is formed of an XMR alloy.

INVENTION SUMMARY

The present invention relates to a radiopaque medical device, such as a stent, for use or implantation in a body lumen. In a preferred embodiment, a radiopaque medical device, such as a stent, is constructed from a tubular-shaped body having a thin wall defining a strut pattern; wherein the tubular body includes a superelastic, nickel-titanium alloy, and the alloy further includes a ternary element selected from the group of chemical elements consisting of iridium, platinum, gold, rhenium, tungsten, palladium, rhodium, tantalum, silver, ruthenium, or hafnium. In a preferred embodiment, the stent according to the present invention has 42.8 atomic percent nickel, 49.7 atomic percent titanium, and 7.5 atomic percent platinum.

As a result, the present invention stent is highly radiopaque as compared to an identical structure made of medical grade stainless steel that is coated with a thin layer of gold. From another perspective, for a given stent having a certain level of radiopacity, the present invention stent having identical dimensions and strut pattern has at least a 10 percent reduction in strut thickness yet maintains that same level of radiopacity.

Self-expanding nitinol stents are collapsed (that is, loaded) and then constrained within a delivery system. At the point of delivery, the stent is released (that is, unloaded) and allowed to return to its original diameter. The stent is designed to perform various mechanical functions within the lumen, all of which are based upon the lower unloading plateau stress. Therefore, it is crucial that the ternary element alloyed with the binary nickel-titanium does not diminish the superelastic characteristics of the nickel-titanium.

To achieve the sufficient degree of radiopacity yet maintaining the superelastic engineering properties of a binary nickel-titanium, preferably, the radiopaque stent of the present invention includes platinum whose atomic percent is greater than or equal to 2.5 and less than or equal to 15. In an alternative embodiment, the nickel-titanium is alloyed with palladium whose atomic percent is greater than or equal to 2.5 and less than or equal to 20. With such compositions, the stress-strain hysteresis curve of the present invention radiopaque nitinol alloy closely approximates the idealized stress-strain hysteresis curve of binary nickel-titanium.

The present invention further contemplates a method for providing a radiopaque nitinol stent. In a preferred embodiment, the method entails providing a tubular-shaped body having a thin wall, wherein the body includes a superelastic nickel-titanium alloy and the alloy further includes a ternary element selected from the group of chemical elements consisting of iridium, platinum, gold, rhenium, tungsten, palladium, rhodium, tantalum, silver, ruthenium, or hafnium; forming a strut pattern; wherein the stent is highly radiopaque. The step of providing a tubular-shaped body includes melting nickel, titanium, and the ternary element and cooling the mixture to form an alloy ingot, hot forming the alloy ingot, hot or cold forming the alloy ingot into a cylinder, drilling the cylinder to form tubing, cold drawing the tubing, and annealing the tubing.

The present invention of course envisions the minor addition of a quaternary element, for example, iron, to further enhance the alloy's formability or its thermomechanical properties. In short, the presence of elements in addition to the ternary elements cited above is contemplated.

In a preferred embodiment, an austenite finish temperature ($A_f$) of the superelastic alloy in the stent is greater than or equal to zero and less than or equal to 37 degrees C. Also in the preferred embodiment, the ingot after melting includes an austenite finish temperature ($A_f$) of greater than or equal to 0 degrees C. and less than or equal to 40 degrees C. The tubing includes an austenite finish temperature ($A_f$) of greater than or equal to −15 degrees C. and less than or equal to 15 degrees C.

Another aspect of the present invention relates to a medical device, such as a stent, that is biocompatible, radiopaque and MRI compatible. In another preferred embodiment, a radiopaque and MRI compatible medical device, such as a stent, is constructed from a tubular-shaped body having a thin wall defining a strut pattern; wherein the tubular body includes a nickel-titanium alloy, and the alloy further includes a ternary element that substitutes for nickel, selected from the group of chemical elements consisting of iridium, platinum, gold, rhenium, tungsten, palladium, rhodium, tantalum, silver, ruthenium, hafnium, osmium, zirconium, niobium, or molybdenum. The weight percent of such a ternary element may by greater than or equal to about 5 and less than or equal to about 70. A preferred embodiment would include nickel and titanium plus either platinum, palladium or tungsten. To provide a stent with a strut thickness ranging from 0.006 inches down to 0.002 inches, the following is the approximate weight percent composition ranges based on theoretical radiopacity equivalent to the Multi-Link Duet stent manufactured by Guidant, for the direct substitution of the precious/refractory metal element for nickel include:

| Minimum composition (weight percent) | Maximum composition (weight percent) |
|---|---|
| 47% Ni—41% Ti—12% Pt | 14% Ni—26% Ti—60% Pt |
| 48% Ni—44% Ti—8% Pd | 6% Ni—32% Ti—62% Pd |
| 49% Ni—43% Ti—8% W | 9% Ni—25% Ti—66% W |

As a result, the present invention stent is both radiopaque and MRI compatible. In some embodiments, these ternary elements depress the transformation temperature such that no stress induced martensite is formed at body temperature. The ternary element can reduce austenite finish temperature ($A_f$) such that the highest temperature at which the martensitic phase can be formed by deformation (designated $M_d$) is below body temperature or 37° C. Additional processing can also be used to fine tune $M_d$. Further, the addition of ternary or even quaternary alloying elements can enhance the ductility of the austenitic phase of a stent.

Other features and advantages of the present invention will become more apparent from the following detailed description of the invention when taken in conjunction with the accompanying exemplary drawings.

BRIEF DESCRIPTION OF THE DRAWINGS

FIG. 1 is a side elevational view, partially in section, depicting a stent mounted on a delivery catheter and expanded within a damaged vessel, pressing a damaged vessel lining against the vessel wall.

FIG. 2 is a side elevational view, partially in section, depicting an expanded stent within the vessel after withdrawal of the delivery catheter.

FIG. 3 is an idealized stress-strain hysteresis curve for a superelastic material.

DETAILED DESCRIPTION OF THE PREFERRED EMBODIMENTS

The present invention relates to a medical device made of radiopaque nitinol. For the sake of illustration, the following exemplary embodiments are directed to stents, although it is understood that the present invention is applicable to other medical devices usable in a body lumen as well.

The stents of the present invention can have virtually any configuration that is compatible with the body lumen in which they are implanted. The stent should preferably be configured so that there is a substantial amount of open area and preferably the open area to metal ratio is at least 80 percent. The stent should also be configured so that dissections or flaps in the body lumen wall are covered and tacked up by the stent.

Figure 4:
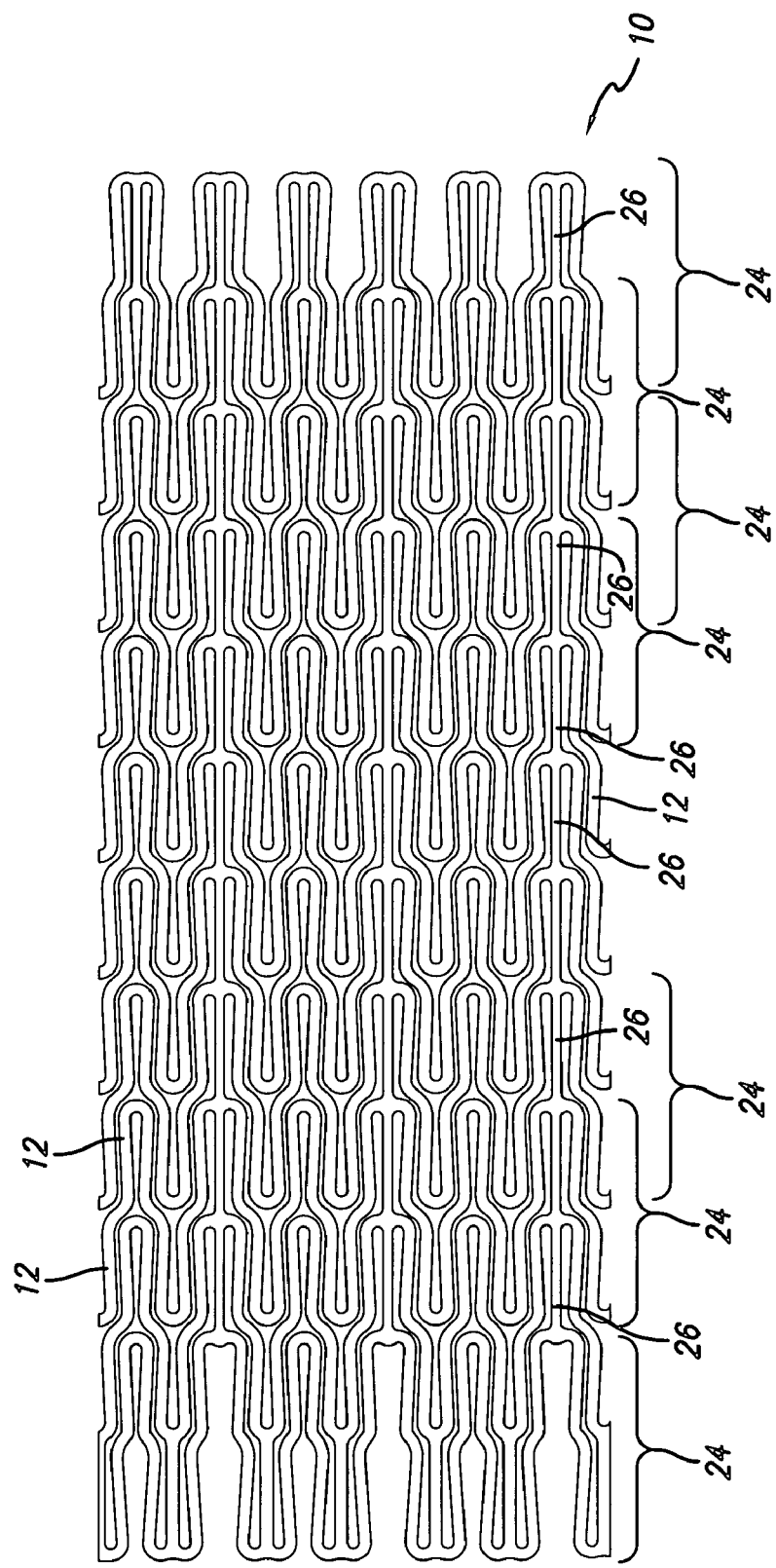
FIG. 4 is a plan view of the flattened strut pattern of an exemplary embodiment superelastic stent.

Referring to FIGS. 1, 2, and 4, in a preferred embodiment, a stent 10 of the present invention is formed partially or completely of alloys such as nitinol (NiTi) which have superelastic (SE) characteristics. Stent 10 is somewhat similar to the stent disclosed in U.S. Pat. No. 5,569,295, "Expandable Stents and Method for Making Same," issued to Lam on Oct. 29, 1996, which patent is incorporated herein by reference. Some differences of the present invention stent from that disclosed in the '295 patent are that the present invention stent is preferably constructed of a superelastic material with the addition of a ternary element, and the strut pattern has changed. Of course, the configuration of the stent 10 is just one example of many stent configurations that are contemplated by the present invention.

Turning to FIG. 4, stent 10 has a tubular form which preferably includes a plurality of radially expandable cylindrical elements 24 disposed generally coaxially and interconnected by members 26 disposed between adjacent cylindrical elements 24. The shapes of the struts 12 forming the strut pattern are designed so they can preferably be nested. This strut pattern is best seen from the flattened plan view of FIG. 4. The serpentine patterned struts 12 are nested such that the extended portions of the struts of one cylindrical element 24 intrude into a complementary space within the circumference of an adjacent cylindrical element. In this manner, the plurality of cylindrical elements 24 can be more tightly packed lengthwise.

As introduced above, an exemplary stent of the present invention includes a superelastic material. In a general sense, superelasticity implies that the material can undergo a large degree of reversible strain as compared to common steel. In a technical sense, the term "superelasticity" and sometimes "pseudoelasticity" refer to an isothermal transformation in nitinol. More specifically, it refers to stress inducing a martensitic phase from an austenitic phase. Alloys having superelastic properties generally have at least two phases: a martensitic phase, which has a relatively low tensile strength and which is stable at relatively low temperatures, and an austenitic phase, which has a relatively high tensile strength and which is stable at temperatures higher than the martensitic phase. Superelastic characteristics generally allow the metal stent to be deformed by collapsing the stent and creating stress which causes the NiTi to reversibly change to the martensitic phase. The stent is restrained in the deformed condition inside a delivery sheath typically to facilitate the insertion into a patient's body, with such deformation causing the isothermal phase transformation. Once within the body lumen, the restraint on the stent is removed, thereby reducing the stress thereon so that the superelastic stent returns towards its original undeformed shape through isothermal transformation back to the austenitic phase. Under these conditions, the stent can be described as self-expanding.

Returning to FIG. 1, the graphic illustrates, in a partial cross-sectional view, the distal end of a rapid exchange stent delivery system that includes a guide wire 14, a delivery sheath 16, and an intravascular catheter 18. For the sake of clarity, the illustration of the delivery system in FIG. 1 has been simplified. It is just one example of a delivery system that may be used with the present invention. More details of a delivery system specifically for use with a self-expanding stent may be found in, for example, U.S. Pat. No. 6,077,295 to Limon et al., entitled "Self-Expanding Stent Delivery System," which is incorporated herein by reference. Other delivery systems such as over-the-wire may be used without departing from the scope of the instant invention.

FIG. 1 further shows an optional expandable balloon 20 inflated through an inflation lumen (not shown), although the balloon is typically not needed for a self-expanding stent.

The stent 10 is first crimped on to the deflated balloon 20, and the entire assembly is kept underneath the delivery sheath 16 until the moment the stent 10 is deployed. The stent 10 is self-expanding so that when the sheath 16 is withdrawn, the stent 10 expands to its larger deployment diameter without assistance from the balloon 20. Nevertheless, some procedures specifically use the balloon 20 to further expand the stent 10 for improved seating in the artery wall 29.

FIG. 2 illustrates the self-expanding stent 10 in the expanded condition after the delivery system has been removed. If an external force is applied to the artery 28, the expanded stent 10 temporarily and at least partially collapses or deforms. As the stent 10 deforms, stress in the nickel-titanium alloy causes an isothermal phase transformation from the austenitic phase to the martensitic phase. When the external force is removed, the stress in stent 10 is likewise diminished so that the stent quickly transforms back from the martensitic phase to the austenitic phase. As this almost instantaneous, isothermal transformation occurs, the stent 10 returns to its fully expanded state and the artery remains open. When the superelastic stent 10 is implanted in an artery 28, its high resilience effectively maintains the patency of the artery while minimizing the risk of permanent arterial collapse at the implant site if the stent is temporarily deformed due to external forces. Furthermore, the resilience of the stent 10 supports the flap 30 to maintain patency of the artery.

Stent 10 is preferably formed from a superelastic material such as nickel-titanium and undergoes an isothermal transformation when stressed if in the austenitic phase. For most purposes, the transformation temperature for the stent 10 is preferably set low enough such that the nickel-titanium alloy is in the austenitic phase while at body temperature.

According to theory, when stress is applied to a specimen of a metal such as nitinol exhibiting superelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase. As the phase transformation progresses, the alloy undergoes significant increases in strain with little or no corresponding increases in stress. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the stress-induced martensite elastically recovers and transforms back to the austenitic phase. The reduction in stress first causes a decrease in strain. As stress reduction reaches the level at which the martensitic phase begins to transform back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as "superelasticity" and sometimes "pseudoelasticity."

FIG. 3 illustrates an idealized stress-strain hysteresis curve for a superelastic, binary nickel-titanium alloy. The relationship is plotted on x-y axes, with the x axis representing strain and the y axis representing stress. For ease of illustration, the x-y axes are labeled on a scale typical for superelastic nitinol, with stress from 0 to 60 ksi and strain from 0 to 9 percent, respectively.

Looking at the plot in FIG. 3, the line from point A to point B represents the elastic deformation of the nickel-titanium alloy. After point B the strain or deformation is no longer proportional to the applied stress and it is in the region between point B and point C that the stress-induced transformation of the austenitic phase to the martensitic phase begins to occur.

At point C moving toward point D, the material enters a region of relatively constant stress with significant deformation or strain. This constant or plateau region is known as the loading stress, since it represents the behavior of the material as it encounters continuous increasing strain. It is in this plateau region C–D that the transformation from austenite to martensite occurs.

At point D the transformation to the martensitic phase due to the application of stress to the specimen is substantially complete. Beyond point D the martensitic phase begins to deform, elastically at first, but, beyond point E, the deformation is plastic or permanent.

When the stress applied to the superelastic metal is removed, the material behavior follows the curve from point E to point F. Within the E to F region, the martensite recovers its original shape, provided that there was no permanent deformation to the martensitic structure. At point F in the recovery process, the metal begins to transform from the stress-induced, unstable, martensitic phase back to the more stable austenitic phase.

In the region from point G to point H, which is also an essentially constant or plateau stress region, the phase transformation from martensite back to austenite takes place. This constant or plateau region G–H is known as the unloading stress. The line from point I to the starting point A represents the elastic recovery of the metal to its original shape.

Binary nickel-titanium alloys that exhibit superelasticity have an unusual stress-strain relationship as just described and as plotted in the curve of FIG. 3. As emphasized above, the superelastic curve is characterized by regions of nearly constant stress upon loading, identified above as loading plateau stress C–D and unloading plateau stress G–H. Naturally, the loading plateau stress C–D always has a greater magnitude than the unloading plateau stress G–H. The loading plateau stress represents the period during which martensite is being stress-induced in favor of the original austenitic crystalline structure. As the load is removed, the stress-induced martensite transforms back into austenite along the unloading plateau stress part of the curve. The difference in stress between the stress at loading C–D and unloading stress G–H defines the hysteresis of the system.

The present invention seeks to preserve the superelastic qualities of nickel-titanium alloys just described yet improve upon the material's radiopacity by addition of a ternary element. This is preferably accomplished in one embodiment by forming a composition consisting essentially of about 30 to about 52 percent titanium and the balance nickel and up to 10 percent of one or more additional ternary alloying elements. Such ternary alloying elements may be selected from the group consisting of iridium, platinum, gold, rhenium, tungsten, palladium, rhodium, tantalum, silver, ruthenium, or hafnium. In the preferred embodiment, the atomic percentage of platinum is greater than or equal to 2.5 and less than or equal to 15. In an alternative embodiment, the atomic percentage of palladium is greater than or equal to 2.5 and less than or equal to 20.

A preferred embodiment stent according to the present invention has 42.8 atomic percent nickel, 49.7 atomic percent titanium, and 7.5 atomic percent platinum. Through empirical studies, the aforementioned compositions produce stent patterns having a radiopacity comparable to the same size and pattern stent made from 316 L stainless steel with a 2.7 to 6.5 μm gold coating.

In various alternative embodiments, the present invention contemplates the minor addition of a quaternary element, for example, iron, to further enhance the alloy's formability or its thermomechanical properties. The presence of impurities such as carbon or oxygen or the like in the present invention alloy is also possible.

A preferred method of fabricating the present invention superelastic, radiopaque metallic stent entails first fashioning nickel-titanium tubing. The tubing is made from vacuum induction melting nickel and titanium with the ternary element according to the compositions suggested above. The ingot is then remelted for consistency. The ingot is next hot rolled into bar stock, then straightened and sized, and hot or cold formed into a cylinder. The cylinder is gun drilled to form the tubing. Instead of gun drilling, other methods of material removal known in the art may be used, including electric discharge machining (EDM), laser beam machining, and the like. Next, the tubing is cold drawn and annealed repeatedly to achieve the finished dimensions.

Any of the foregoing preferred embodiment steps may be repeated, taken out of sequence, or omitted as necessary depending on desired results. From here on, the tubing follows conventional stent fabrication techniques such as laser cutting the strut pattern, heat setting, etc.

The following are additional processing guide posts for the present invention to achieve a sufficiently radiopaque stent yet maintaining the superelastic stress-strain behavior of the alloy. Empirical evidence suggests that, in various preferred embodiments, a Ni—Ti—Pd or Ni—Ti—Pt ingot should have the following austenite finish temperature: 0 degrees $C \leq A_f \leq 40$ degrees C. The Ni—Ti—Pd or Ni—Ti—Pt tubing should exhibit an austenite finish temperature of: $-15$ degrees $C \leq A_f \leq 15$ degrees C. In an exemplary embodiment, the final laser cut Ni—Ti—Pd or Ni—Ti—Pt stent should exhibit an austenite finish temperature of: 0 degrees $C \leq A_f \leq 37$ degrees C. Of course, the $A_f$ of the finished laser cut stent can be set as needed by various heat treating processes known in the art.

It is understood that the austenite finish temperature ($A_f$) is defined to mean the temperature at which the material completely reverts to austenite. In technical terms, the $A_f$ (and other transformation temperatures $A_s$, $M_s$, $M_f$) as it applies to an ingot made of Ni—Ti—Pd or Ni—Ti—Pt, for example, is determined by a Differential Scanning Calorimeter (DSC) test, known in the art. The DSC test method to determine transformation temperatures for the ingot is guided by ASTM standard no. F 2004-00, entitled "Standard Test Method For Transformation Temperature Of Nickel-Titanium Alloys By Thermal Analysis."

The "active $A_f$" for the tubing and the finished stent is determined by a bend and free recovery test, also known in the art. In such a test, the tubing is cooled to under the Mf temperature, deformed, and warmed up. While monitoring the increasing temperature, the point of final recovery of the deformation in the tubing approximates the $A_f$ of the material. The active $A_f$ testing technique is guided by a second ASTM standard entitled "Standard Test Method For Determination Of Transformation Temperature Of Nickel-Titanium Shape Memory Alloys By Bend And Free Recovery," or by equivalent test methods known in the art.

Samples of wire made in accordance with the foregoing exemplary embodiments were tested. Specifically, the stress-strain relationship based on empirical data for nickel-titanium-palladium and nickel-titanium-platinum are plotted against binary nitinol in FIG. 5. Curve A corresponds to a sample of nickel-titanium-platinum. Curve B is based on a sample of binary nitinol. Curve C is based on a sample of nickel-titanium-palladium. To generate the empirical data, the wire samples were placed under increasing tension until past the phase transformation from their initial austenitic phase to their martensitic phase. Tension was then slowly released prior to any plastic deformation until stress on the samples dropped to zero with full deformation recovery.

Figure 5:
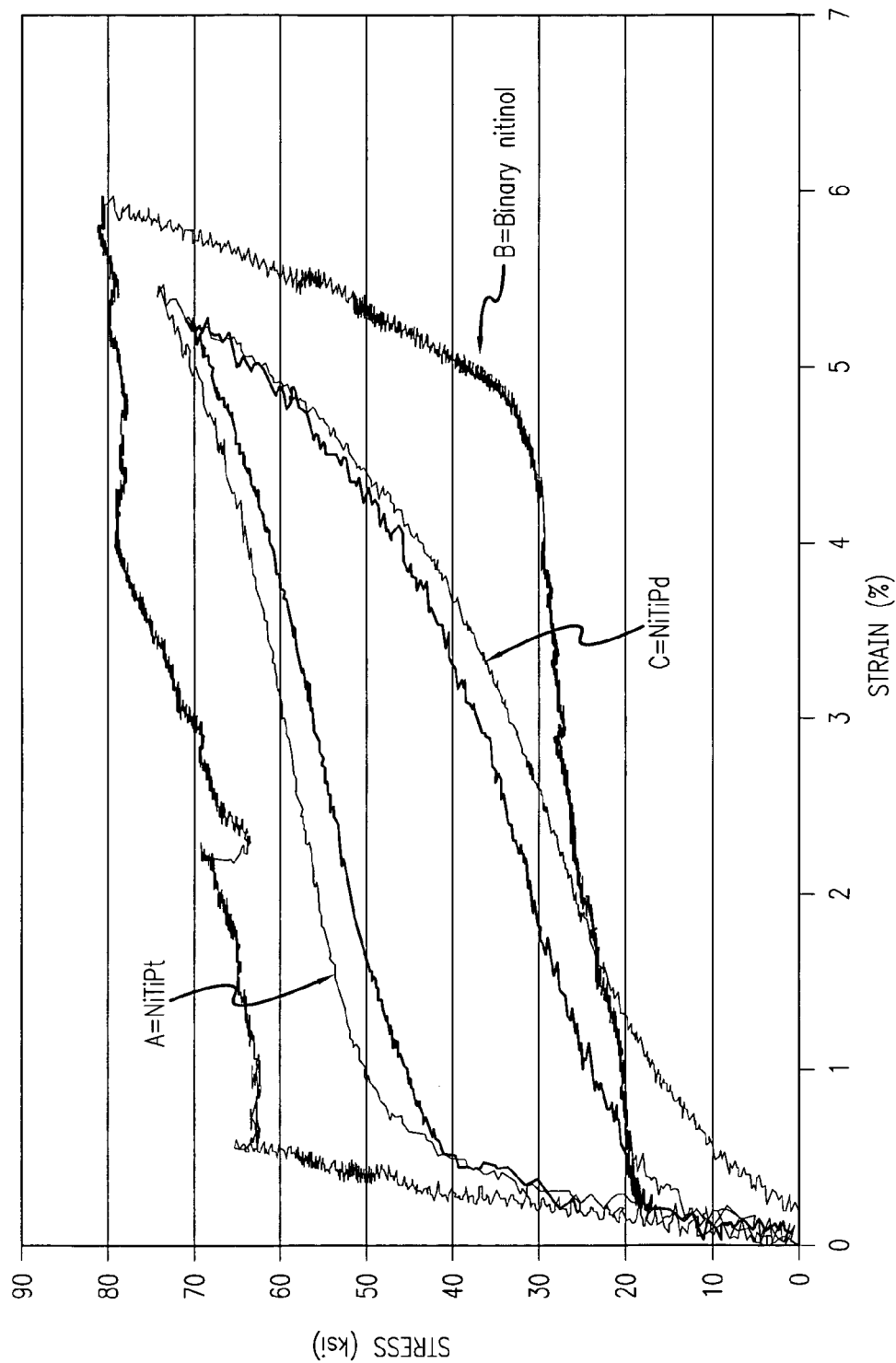
FIG. 5 is a group of empirical data curves illustrating the highly similar stress-strain relationships among binary nitinol and the nickel-titanium-palladium and nickel-titanium-platinum alloys used in the present invention.

As is apparent from the plot of FIG. 5, the present invention nickel-titanium-palladium and nickel-titanium-platinum alloys have stress-strain curves that closely follow the hysteresis curve for binary nitinol. All three curves have essentially flat loading and unloading plateau stresses indicating the presence of a phase transformation that is characteristic of superelastic metals. Hence, the present invention nitinol stent incorporates a ternary element, in these exemplary embodiments palladium or platinum, to improve radiopacity yet the materials' superelastic capability is preserved. What has been missing heretofor is empirical evidence that this level of radiopacity can be achieved while preserving the superelastic characteristics of these alloys.

The present invention further provides a nitinol stent having improved radiopacity without reliance on increasing the stent wall thickness or strut thickness. Increasing wall or strut thicknesses detracts from the flexibility of the stent, which is detrimental to deliverability. Rather, the present invention superelastic nitinol stent has a thin wall/strut thickness and/or strut cross-sectional area akin to a conventional stainless steel stent, and has comparable radiopacity to a stainless steel stent with a thin coating of gold. The wall/strut thickness is defined by the difference between the inside diameter and the outside diameter of the tube.

Indeed, the improved radiopacity of the present invention stent can be characterized strictly by strut thickness. In this context, the present invention radiopaque stent has a reduced strut thickness yet exhibits the radiopacity of an identical stent having thicker struts. In other words, given a stent exhibiting a certain level of radiopacity, the present invention stent having the identical dimensions and strut pattern achieves that level of radiopacity yet it has at least a 10 percent reduction in strut thickness as compared to the reference stent.

Alternatively, the 10 percent reduction can also be quantified in terms of the cross-sectional area of the strut. That is, for a given stent having a certain level of radiopacity with struts with a given cross-sectional area, the present invention stent having the same dimensions and strut pattern achieves the same level of radiopacity but has struts with at least a 10 percent reduction in cross-sectional area as compared to the reference stent.

Another aspect of nitinol aside from its superelasticity is shape memory. The present invention can also be employed with respect to this physical attribute as described below.

The shape memory effect allows a nitinol structure to be deformed to facilitate its insertion into a body lumen or cavity, and then heated within the body so that the structure returns to its original, set shape. Nitinol alloys having shape memory effect generally have at least two phases: a martensitic phase, which has a relatively low tensile strength and which is stable at relatively low temperatures, and an austenitic phase, which has a relatively high tensile strength and which is stable at temperatures higher than the martensitic phase.

Shape memory effect is imparted to the alloy by heating the nickel-titanium metal to a temperature above which the transformation from the martensitic phase to the austenitic phase is complete; i.e., a temperature above which the austenitic phase is stable. The shape of the metal during this heat treatment is the shape "remembered." The heat-treated metal is cooled to a temperature at which the martensitic phase is stable, causing the austenitic phase to transform to the martensitic phase. The metal in the martensitic phase is then plastically deformed, e.g., to facilitate the entry thereof into a patient's body. Subsequent heating of the deformed martensitic phase to a temperature above the martensite to austenite transformation temperature causes the deformed martensitic phase to transform to the austenitic phase. During this phase transformation the metal reverts back towards its original shape.

The recovery or transition temperature may be altered by making minor variations in the composition of the metal and in processing the material. In developing the correct composition, biological temperature compatibility must be determined in order to select the correct transition temperature. In other words, when the stent is heated, it must not be so hot that it is incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," *Scientific American*, Vol. 281, pp. 74–82 (November 1979), incorporated herein by reference.

Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It is desirable to have the transition temperature set at just below body temperature to insure a rapid transition from the martinsitic state to the austenitic state when the stent is implanted in a body lumen.

Turning again to FIGS. 1, 2, and 4, the present invention stent 10 is formed from a shape memory alloy, such as NiTi discussed above. After the stent 10 is inserted into an artery 28 or other vessel, the delivery sheath 16 is withdrawn exposing the stent 10 to the ambient environment. The stent 10 then immediately expands due to contact with the higher temperature within artery 28 as described for devices made from shape memory alloys. An optional expandable balloon 20 may be inflated by conventional means to further expand the stent 10 radially outward.

Again, if an external force is exerted on the artery, the stent 10 temporarily at least partially collapses. But the stent 10 then quickly regains its former expanded shape due to its shape memory qualities. Thus, a crush-resistant stent, having shape memory characteristics, is implanted in a vessel. It maintains the patency of a vessel while minimizing both the risk of permanent vessel collapse and the risk of dislodgment of the stent from the implant site if the stent is temporarily deformed due to external forces.

When the stent 10 is made in accordance with the present invention, it is also highly radiopaque. The same alloying processes described earlier are used here to add the ternary element to increase the radiopacity of the stent. Insofar as the martensitic to austenitic phase transformation is thermally driven, the deployment of the present invention stent can be explained in terms of the shape memory effect.

Another aspect of the present invention relates to a stent that is biocompatible, radiopaque and MRI compatible. In another preferred embodiment, a radiopaque and MRI compatible stent is constructed from a tubular-shaped body having a thin wall defining a strut pattern; wherein the tubular body includes a nickel-titanium alloy, and the alloy further includes a ternary element that substitutes for nickel, selected from the group of chemical elements consisting of iridium, platinum, gold, rhenium, tungsten, palladium, rhodium, tantalum, silver, ruthenium, hafnium, osmium, zirconium, niobium, or molybdenum. A composition may be formed including nickel, titanium, and between about 5% and about 70% of one or more of these additional ternary alloying elements. A preferred embodiment would include nickel and titanium plus either platinum, palladium or tungsten. In one preferred embodiment, the weight percent of platinum is greater than or equal to about 12 and less than or equal to about 60. In another preferred embodiment, the weight percent of palladium is greater than or equal to about 8 and less than or equal to about 62. In yet another preferred embodiment, the weight percent of tungsten is greater than or equal to about 8 and less than or equal to about 66.

The stent of this embodiment may not have the superelastic qualities of nitinol because of the lower weight percent of nickel and/or titanium in the XMR alloy. If the composition of the XMR alloy is such that it has no superelastic qualities of nitinol, then the XMR alloy will not be suitable for self-expanding stents. However, this XMR alloy without the superelastic qualities of nitinol can benefit a balloon expandable stent.

To provide a stent with a strut thickness ranging from about 0.006 inches down to about 0.002 inches, the following (produced as Table 1) is the approximate weight percent composition ranges based on theoretical radiopacity equivalent to the Multi-Link Duet stent manufactured by Guidant, for the direct substitution of the precious/refractory metal element for nickel include:

TABLE 1

| Minimum composition (weight percent) | Maximum composition (weight percent) |
|---|---|
| 47% Ni—41% Ti—12% Pt | 14% Ni—26% Ti—60% Pt |
| 48% Ni—44% Ti—8% Pd | 6% Ni—32% Ti—62% Pd |
| 49% Ni—43% Ti—8% W | 9% Ni—25% Ti—66% W |

In one study, a wire having a composition of 39Ni—38Ti—23Pt by weight was annealed in argon to place it in the austenitic phase. Tensile tests of this wire were conducted, and the results are shown in Table 2 below, in comparison to a fully annealed 316L stainless steel wire ("FA 316L S.S."). The wire data for the FA 316L S.S. wire was taken from Fort Wayne Metals website at www.fortwaynemetals.com.

TABLE 2

| Alloy | Yield Strength | Ultimate Tensile Strength | Elongation |
|---|---|---|---|
| 39Ni—38Ti—23Pt | 85 ksi | 105 ksi | 34% |
| FA 316L S.S. | 45 ksi | 91 ksi | 42% |

The above data for the 39Ni—38Ti—23Pt composition wire indicates that the mechanical properties for this alloy are acceptable for use as a balloon expandable stent.

Figure 6:
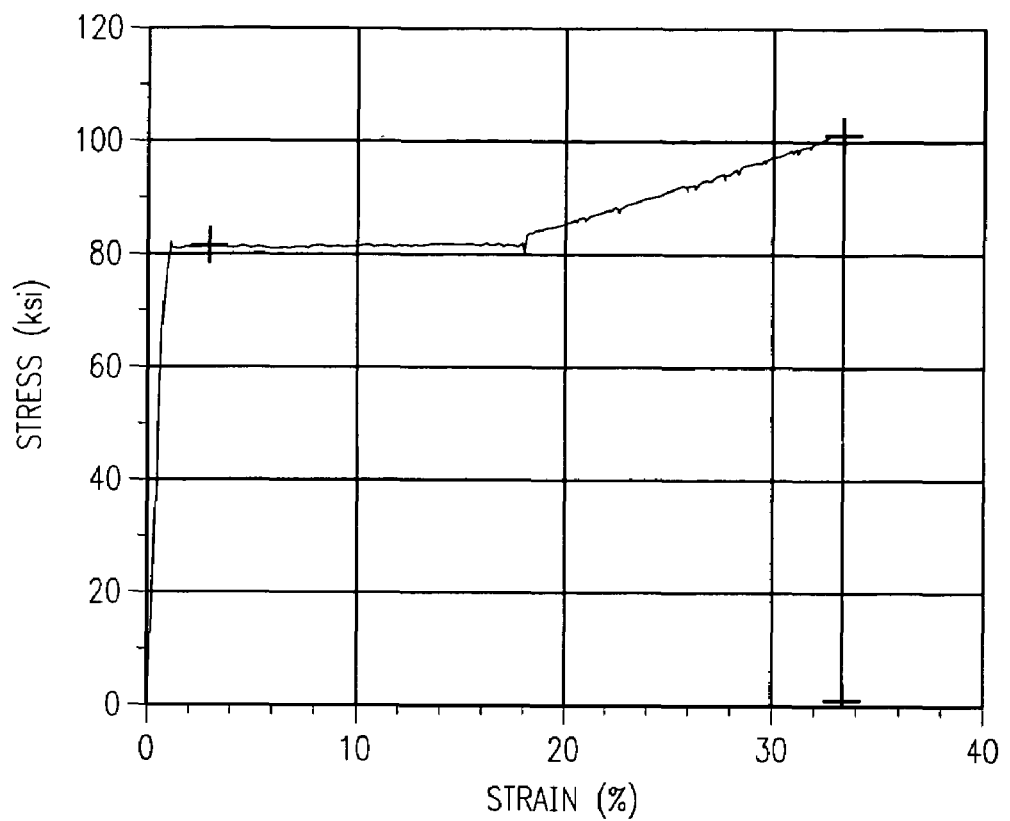
FIG. 6 illustrates a tensile test curve of a nickel-titanium-platinum alloy of the present invention at room temperature.

Referring now to FIG. 6, a tensile test curve is shown of the 39Ni—38Ti—23Pt composition wire at room temperature. The curve shows a sharp yield point followed by an elongation at a constant stress. The curve shows that the lower yield strength is 81.3 ksi, the ultimate tensile strength is 100.6 ksi, and the elongation is 33.2%. A theory behind the upper-lower yield point phenomenon holds that solute atoms moving with dislocations in the material prevent an immediate onset of traditional plastic deformation. The phenomenon is associated with a visual surface deformation artifact called Lüders bands or stretcher stains, where visually obvious bands form across the surface of the test specimen. This phenomenon should not affect the functionality of the finished device. The theory of the upper-lower yield point phenomenon is discussed in G. E. Dieter, Mechanical Metallurgy, $2^{nd}$ ed., McGraw-Hill Book Co., pp. 204–208, and in R. E. Reed-Hill, Physical Metallurgy Principles, D. Van Nostrand Co., Inc., Princeton, N.J., pp. 231–234.

The MRI compatibility of nitinol is generally accepted in the industry. While magnetic susceptibility properties are not additive in an absolute sense, adding elements with low magnetic susceptibility values to nitinol should maintain the MRI compatibility of the alloy under discussion here. It should be noted that nickel by itself is ferromagnetic, and yet in combination with titanium it has excellent MRI compatibility. Table 3 below shows measured magnetic susceptibility values for 316L stainless steel, which is MRI safe but not MRI compatible, nitinol, and the 39Ni—38Ti—23Pt alloy discussed above. It also shows literature values for elements under disclosure here for possible addition to nitinol to manufacture a radiopaque, MRI compatible medical device. The literary values were taken from CRC Handbook of Chemistry and Physics, RC Press, $63^{rd}$ Ed. 1982, and Schenck J F, *Med Phys.* 23(6), June 1996.

TABLE 3

| Alloy/Element | Magnetic Susceptibility (SI $\times 10^{-6}$) |
|---|---|
| 316L stainless steel | 3024 |
| Nitinol | 237 |
| 39-Ni—38Ti—23Pt | 167 |
| Iridium | 38 |
| Nickel | ferromagnetic |
| Osmium | 15 |
| Platinum | 279 |
| Palladium | 813 |
| Rhodium | 168 |
| Ruthenium | 67 |
| Hafnium | 70 |
| Molybdenum | 119 |
| Niobium | 226 |
| Rhenium | 96 |
| Tantalum | 178 |
| Titanium | 182 |
| Tungsten | 82 |
| Zirconium | 109 |

The alloy having a composition of the present invention can be used with any medical device, especially medical devices that require either radiopacity or MRI compatibility. In some embodiments, these ternary elements depress the transformation temperature such that no stress induced martensite is formed at body temperature. The ternary element can reduce austenite finish temperature ($A_f$) such that $M_d$ is below body temperature or 37° C. Additional processing can also be used to fine tune $M_d$. Further, the addition of ternary or even quaternary alloying elements can enhance the ductility of the austenitic phase of a stent.

While the present invention has been illustrated and described herein in terms of a radiopaque nitinol stent, it is apparent to those skilled in the art that the present invention can be used in other instances. Other modifications and improvements may be made without departing from the scope of the present invention.

We claim:

1. A medical device for use in a body lumen, comprising a tubular-shaped body having a wall defining a pattern of struts, wherein the tubular-shaped body comprises a nickel-titanium alloy, said nickel-titanium alloy further comprising at least one ternary element chosen from platinum and palladium, and wherein said struts have a thickness ranging from about 0.002 inches to about 0.006 inches.

2. The medical device of claim 1, wherein the tubular-shaped body is a stent.

3. The medical device of claim 2, wherein the device is radiopaque and MRI compatible.

4. The medical device of claim 1, wherein the at least one ternary element is present in the alloy in an amount ranging from about 5 to about 70 weight percent.

5. The medical device of claim 4, wherein the at least one ternary element is platinum, which is present in an amount ranging from about 5 to about 60 weight percent.

6. The medical device of claim 4, wherein the at least one ternary element is palladium, which is present in an amount ranging from about 5 to about 62 weight percent.

7. The medical device of claim 1, wherein the at least one ternary element is platinum, which is present in an amount ranging from about 2.5 to about 15 weight percent.

8. The medical device of claim 1, wherein the at least one ternary element is palladium, which is present in an amount ranging from about 2.5 to about 20 weight percent.

9. The medical device of claim 1, wherein the tubular-shaped body comprises a superelastic alloy.

10. The medical device of claim 1, wherein the tubular-shaped body comprises a non-superelastic alloy.

11. The medical device of claim 1, wherein the device is radiopaque and MRI compatible.

12. The medical device of claim 4, wherein the device is radiopaque and MRI compatible.

13. The medical device of claim 1, wherein the tubular-shaped body is in an austenitic phase at body temperature.

14. The medical device of claim 1, wherein said alloy further comprises at least one quaternary element.

15. A medical device for use in a body lumen, comprising a tubular-shaped body having a wall defining a pattern of struts, wherein the tubular-shaped body comprises a non-superelastic nickel-titanium alloy, said non-superelastic alloy further comprising at least one ternary element chosen from iridium, platinum, gold, rhenium, tungsten, palladium, rhodium, tantalum, silver, ruthenium, hafnium, osmium, zirconium, niobium, and molybdenum, and wherein said struts have a thickness ranging from about 0.002 inches to about 0.006 inches.

16. The medical device of claim 15, wherein said tubular-shaped body is a stent.

17. The medical device of claim 15, wherein the at least one ternary element is chosen from platinum, palladium, and tungsten.

18. The medical device of claim 17, wherein the ternary element is chosen from platinum and palladium.

19. The medical device of claim 18, wherein the at least one ternary element is palladium, which is present in an amount ranging from about 2.5 to about 20 weight percent.

20. The medical device of claim 15, wherein the at least one ternary element is present in the alloy in an amount ranging from about 5 to about 70 percent by weight.

21. The medical device of claim 20, wherein the at least one ternary element is platinum, which is present in an amount ranging from about 5 to about 60 weight percent.

22. The medical device of claim 20, wherein the at least one ternary element is palladium, which is present in an amount ranging from 5 to 62 weight percent.

23. The medical device of claim 20, wherein the ternary element is tungsten, which is present in an amount ranging from about 8 to about 66 weight percent.

24. The medical device of claim 15, wherein the at least one ternary element is platinum, which is present in an amount ranging from about 2.5 to about 15 weight percent.

25. The medical device of claim 15, wherein the tubular-shaped body is in an austenitic phase at body temperature.

26. The medical device of claim 15, wherein said alloy further comprises at least one quaternary element.

27. A medical device for use in a body lumen, comprising a tubular-shaped body having a wall defining a pattern of struts, wherein the tubular-shaped body comprises a superelastic nickel-titanium alloy, said superelastic alloy further comprising at least one ternary element chosen from iridium, platinum, rhenium, palladium, rhodium, silver, ruthenium, osmium, zirconium, and molybdenum, and wherein said struts have a thickness ranging from about 0.002 inches to about 0.006 inches.

28. The medical device of claim 27, wherein said tubular-shaped body is a stent.

29. The medical device of claim 27, wherein the at least one ternary element is chosen from platinum and palladium.

30. The medical device of claim 29, wherein the ternary element is platinum, which is present in an amount ranging from about 2.5 to about 15 weight percent.

31. The medical device of claim 29, wherein the ternary element is palladium, which is present in an amount ranging from about 2.5 to about 20 weight percent.

32. The medical device of claim 27, wherein the at least one ternary element is present in the alloy in an amount ranging from about 5 to about 70 percent by weight.

33. The medical device of claim 32, wherein the ternary element is platinum, which is present in an amount ranging from about 5 to about 60 weight percent.

34. The medical device of claim 32, wherein the ternary element is palladium, which is present in an amount ranging from about 5 to about 62 weight percent.

35. The medical device of claim 27, wherein the tubular-shaped body is in an austenitic phase at body temperature.

36. The medical device of claim 27, wherein said alloy further comprises at least one quaternary element.

37. An MRI compatible and radiopaque stent for use in a body lumen, wherein said stent comprises a tubular-shaped body having a wall defining a pattern of struts, wherein said struts have a thickness ranging from about 0.002 inches to about 0.006 inches, and a superelastic, radiopaque, and MRI compatible alloy, said superelastic alloy comprising nickel-titanium and from about 5 to about 70 weight percent of a ternary element chosen from iridium, platinum, rhenium, palladium, rhodium, silver, ruthenium, osmium, zirconium, and molybdenum.

38. The MRI compatible and radiopaque stent of claim 37, wherein said ternary element is chosen from platinum and palladium.

39. The MRI compatible and radiopaque stent of claim 37, wherein the tubular-shaped body is in an austenitic phase at body temperature.

40. The medical device of claim 37, wherein said alloy further comprises at least one quaternary element.

41. An MRI compatible and radiopaque stent for use in a body lumen, wherein said stent comprises a tubular-shaped body having a wall defining a pattern of struts, wherein said struts have a thickness ranging from about 0.002 inches to about 0.006 inches, and a non-superelastic, radiopaque, and MRI compatible alloy, said non-superelastic alloy comprising nickel-titanium and from about 5 to about 70 weight percent of a ternary element chosen from iridium, platinum, gold, rhenium, tungsten, palladium, rhodium, tantalum, silver, ruthenium, hafnium, osmium, zirconium, niobium, and molybdenum.

42. The MRI compatible and radiopaque stent of claim 41, wherein said ternary element is chosen from platinum and palladium.

43. The MRI compatible and radiopaque stent of claim 41, wherein the tubular-shaped body is in an austenitic phase at body temperature.

44. The medical device of claim 41, wherein said alloy further comprises at least one quaternary element.

45. An MRI compatible and radiopaque stent for use in a body lumen, wherein said stent comprises a superelastic, radiopaque, and MRI compatible alloy, said superelastic alloy comprising nickel-titanium, from about 5 to about 70 weight percent of a ternary element chosen from iridium, platinum, rhenium, palladium, rhodium, silver, ruthenium, osmium, zirconium, and molybdenum, and at least one quaternary element.

46. The MRI compatible and radiopaque stent of claim 45, wherein the superelastic alloy is in an austenitic phase at body temperature.

47. The MRI compatible and radiopaque stent of claim 45, wherein the at least one ternary element is chosen from platinum and palladium.

48. An MRI compatible and radiopaque stent for use in a body lumen, wherein said stent comprises a non-superelastic, radiopaque, and MRI compatible alloy, said non-superelastic alloy comprising nickel-titanium, from about 5 to about 70 weight percent of a ternary element chosen from iridium, platinum, gold, rhenium, tungsten, palladium, rhodium, tantalum, silver, ruthenium, hafnium, osmium, zirconium, niobium, and molybdenum, and at least one quaternary element.

49. The MRI compatible and radiopaque stent of claim 48, wherein the at least one ternary element is chosen from platinum and palladium.

\* \* \* \* \*

UNITED STATES PATENT AND TRADEMARK OFFICE
CERTIFICATE OF CORRECTION

PATENT NO. : 7,128,757 B2
APPLICATION NO. : 10/814326
DATED : October 31, 2006
INVENTOR(S) : Boylan et al.

It is certified that error appears in the above-identified patent and that said Letters Patent is hereby corrected as shown below:

Claim 7, col. 14, line 41, "platinum" should read --palladium--.

Signed and Sealed this

Twenty-third Day of January, 2007

JON W. DUDAS
*Director of the United States Patent and Trademark Office*